(12) United States Patent
Williams et al.

(10) Patent No.: US 6,210,972 B1
(45) Date of Patent: Apr. 3, 2001

(54) CHARACTERIZATION OF FLOWING DISPERSIONS

(75) Inventors: Richard Andrew Williams, Falmouth; Fraser John Dickin, Goostrey, both of (GB)

(73) Assignee: Disperse Technologies Limited (GB)

( * ) Notice: Subject to any disclaimer, the term of this patent is extended or adjusted under 35 U.S.C. 154(b) by 0 days.

(21) Appl. No.: 09/065,071

(22) PCT Filed: Oct. 24, 1996

(86) PCT No.: PCT/GB96/02602

§ 371 Date: Jun. 9, 1998

§ 102(e) Date: Jun. 9, 1998

(87) PCT Pub. No.: WO97/15825

PCT Pub. Date: May 1, 1997

(30) Foreign Application Priority Data

Oct. 27, 1995 (GB) .................................................. 9522060

(51) Int. Cl.[7] .................................................. G01N 27/06
(52) U.S. Cl. ................... 436/150; 73/861.08; 324/600; 324/686; 324/688; 324/691; 422/98; 436/151
(58) Field of Search ..................... 436/150, 151; 422/98; 204/412, 416; 324/600, 691, 686, 688; 73/861.08

(56) References Cited

U.S. PATENT DOCUMENTS

| 3,174,922 | * | 3/1965 | Berry et al. | 324/686 |
| 3,347,768 | * | 10/1967 | Clark et al. | 204/196.01 |
| 4,533,457 | * | 8/1985 | Watanabe | 204/416 |
| 4,758,325 | * | 7/1988 | Kanno et al. | 204/416 |
| 4,897,173 | * | 1/1990 | Nankai et al. | 204/403 |
| 5,104,639 | * | 4/1992 | Matson | 436/150 |
| 5,208,544 | * | 5/1993 | McBrearty et al. | 324/688 |
| 5,291,791 | * | 3/1994 | Lucas et al. | 73/861.08 |
| 5,576,617 | * | 11/1996 | Webb et al. | 73/861.08 |

FOREIGN PATENT DOCUMENTS

| 0 172 616 A2 | 2/1986 | (EP) . |
| 0 514 964 A2 | 11/1992 | (EP) . |
| 95/24155 | 9/1995 | (WO) . |

OTHER PUBLICATIONS

Microelectrical tomography of flowing colloidal dispersions and dynamic interfaces, R.A. Williams et al, The Chemical Engineering Journal, 56 (1995) Month Unavailable 143–148.

Pp. 771–773 of *Electronics Letters*, M. Wang et al, "Electrical Resistance Tomography of Metal Walled Vessels and Pipelines", May 12, 1994, vol. 30, No. 10.

* cited by examiner

Primary Examiner—T. Tung
(74) Attorney, Agent, or Firm—Renner, Otto, Boisselle & Sklar, LLP (57) ABSTRACT

A microelectrical resistance tomography system comprising one or more sensors, each sensor including a wafer substrate of electrically insulating material having an aperture bounding a fluid flow path through a tube and a plurality of sensor electrodes on the substrate disposed circumferentially around the aperture so as to contact the fluid.

37 Claims, 8 Drawing Sheets

FIG.1

(a) HOMOGENEOUS (b) CONDUCTING PROBE (c) INSULATING PROBE

EXAMPLES OF STANDARD MESH USED FOR RECONSTRUCTION

FIG. 4

EXAMPLES OF DYNAMIC MESH USED FOR RECONSTRUCTION

FIG. 5

RAW RECONSTRUCTION IMAGE
AT INSTANT OF TIME (a)

RESOLVED BOUNDARY OF
PARTICULATE AT INSTANT OF TIME (b)

SIDE VIEW SHOWING SEQUENTIAL STACKED IMAGES.

(c)

VISUALISATION OF
PARTICLES FROM
WHICH VOLUME,
SIZE AND SHAPE
CAN BE
MEASURED.

2D CONTOUR MAP AT INSTANT OF TIME (a)

(b)

DISTRIBUTION OF VOXEL CONDUCTIVITY

ELECTRODE CONFIGURATION

REAR SIDE OF POLYMER FILM

PROCESS FLUID

POLYMER FILM ROLLED AND SEALD FOR INSERTION INSIDE OF PIPE

CHARACTERIZATION OF FLOWING DISPERSIONS

This invention relates to an apparatus and methods for characterizing the properties of a multiphase dispersion flowing through a tube, for example, for measuring the size and concentration of solid particulates suspended in a liquid phase, and including the use of such information for monitoring and controlling dispersion manufacturing processes.

The dispersion would normally consist of one discontinuous phase (solid, gas or liquid) present in the form of particles, droplets or bubbles mixed in a second continuous phase (normally, a liquid). It is desirable to be able to measure-on-line and continuously, the characteristics of the mixture (size and size distribution of the discontinuous phase, the number concentration of discontinuous phase, the velocity of the discontinuous phase etc) since these determine the properties of the mixture.

Such mixtures are commonplace in many types of manufacturing processes in the form of emulsions, colloidal dispersions and suspensions, and are widely utilised in the cosmetics, food, pharmaceutical, medical, detergents, chemical, minerals, nuclear. biotechnical, ceramics, paper and environmental sectors. For instance, the production of liquid-liquid emulsions in which the discontinuous phase is often oil-based and the continuous phase is aqueous-based requires careful control. One specific example is the production of a food (mayonnaise) emulsion in which control of the droplet size is crucial to the shelf-life and taste of the product and the ease of use for the consumer. Changes in manufacturing conditions (addition of chemical reagents or different hydrodynamic conditions) can change the droplet size distribution or alter the kinetics of coagulation or cause breakage of the droplets during processing. The present invention provides a means of monitoring such properties routinely thus allowing the data so generated to be used to control the manufacturing process and also further allow correlation of the emulsion properties to the customers perception of the product.

Conventional measurement methods for monitoring the size of particulates of this type (in the size range 0.5–1000 microns) normally use ex-situ methods, requiring removal of a sample from the process stream. Common methods include light-scattering, x-ray absorption or particle counting using electrical zone sensors (T Allen, Particle Size Measurement. 4th edn., Chapman & Hall, London, 1990). The samples so removed often have to be further prepared for analysis by diluting the dispersion with additional continuous phase, which may alter the dispersion properties and which introduces further sampling error, and is time consuming.

The present invention facilitates the in-situ characteristic of the properties of a multiphase dispersion.

The present invention also permits in-situ derivation of the size distribution and the shape distribution of the dispersed phase.

Further, the present invention allows such measurements to be performed on dispersions moving within tubes or conduits of small diameter (less than ca. 10 mm).

Further still, the present invention provides two and three dimensional imaging of multiphase dispersions.

The present invention also permits the structure of flowing dispersions to be discerned for quality assessment and process control processes.

According to a first aspect of the invention there is provided a microelectrical resistance tomography sensor comprising a substrate of electrically insulating material and having an aperture bounding a fluid flow path and sensor electrodes on the substrate disposed around the aperture so as to contact fluid in the flow path and connected to a cable connector on the substrate.

The sensor electrodes may be disposed regularly around the aperture.

The sensor electrodes may extend into the aperture and alone the flow path.

The aperture may be circular.

The sensor electrodes may be printed on to the substrate.

The sensor may comprise guard electrodes which stand between sensor electrodes. The guard electrodes may terminate short of flow path fluid contact.

The guard electrodes may be electrically connected, and may be earthed.

The substrate may comprise a wafer of uniform thickness and may be adapted for clamping between pipe sections defining the fluid flow path. The sensor may have apertures displaced from the fluid flow path bounding aperture.

According to a second aspect of the invention there is provided a sensor arrangement for microelectrical resistance tomography comprising a plurality of sensors according to the first aspect of the invention disposed along said fluid flow path.

The sensors may have similar electrode configurations, which may be aligned.

According to a third aspect of the invention there is provided a microelectrical resistance tomography system comprising a sensor according to the first aspect of the invention or a sensor arrangement according to the second aspect of the invention, in a tube, flow means to flow a fluid under investigation past the sensor or arrangement and electrical control and measurement means adapted to apply selectively oscillating current to the sensor electrodes and measure electric potentials across the sensor electrodes.

The system may comprise fluid flow control means adapted to control fluid flow through the tube.

The system may comprise analysis means adapted to analyse the electric potentials measured by the control and measurement means. The analysis means may comprise tomographic "image" store means adapted to store a succession of tomographic images of a flowing fluid.

The analysis means may comprise computer means evaluating image data in accordance with predetermined algorithms.

The analysis means may comprise a neural net.

According to a fourth aspect of the invention there is provided a method for characterizing a non-homogeneous flowing material in which the material is passed through a tube having a plurality of electrodes disposed around the flow, oscillating current is injected into the flow via selected ones of the electrodes and the voltage response on other electrodes is measured.

A plurality of measurements may be made using different selected electrodes for current injection and/or measurement. All possible combinations of electrodes may be used for current injection and measurement to give a plurality of measurements.

The different measurements may be effected within a time interval which is small in comparison with the time taken for a particle in the flow to pass through the measurement region.

A tomographic image may be derived from the plurality of measurements. A plurality of such tomographic images may be derived at predetermined time intervals.

The plurality of measurements, or quantities related to or derived therefrom, may be analysed by a neural net.

BRIEF DESCRIPTION OF THE DRAWINGS

Figure 1:
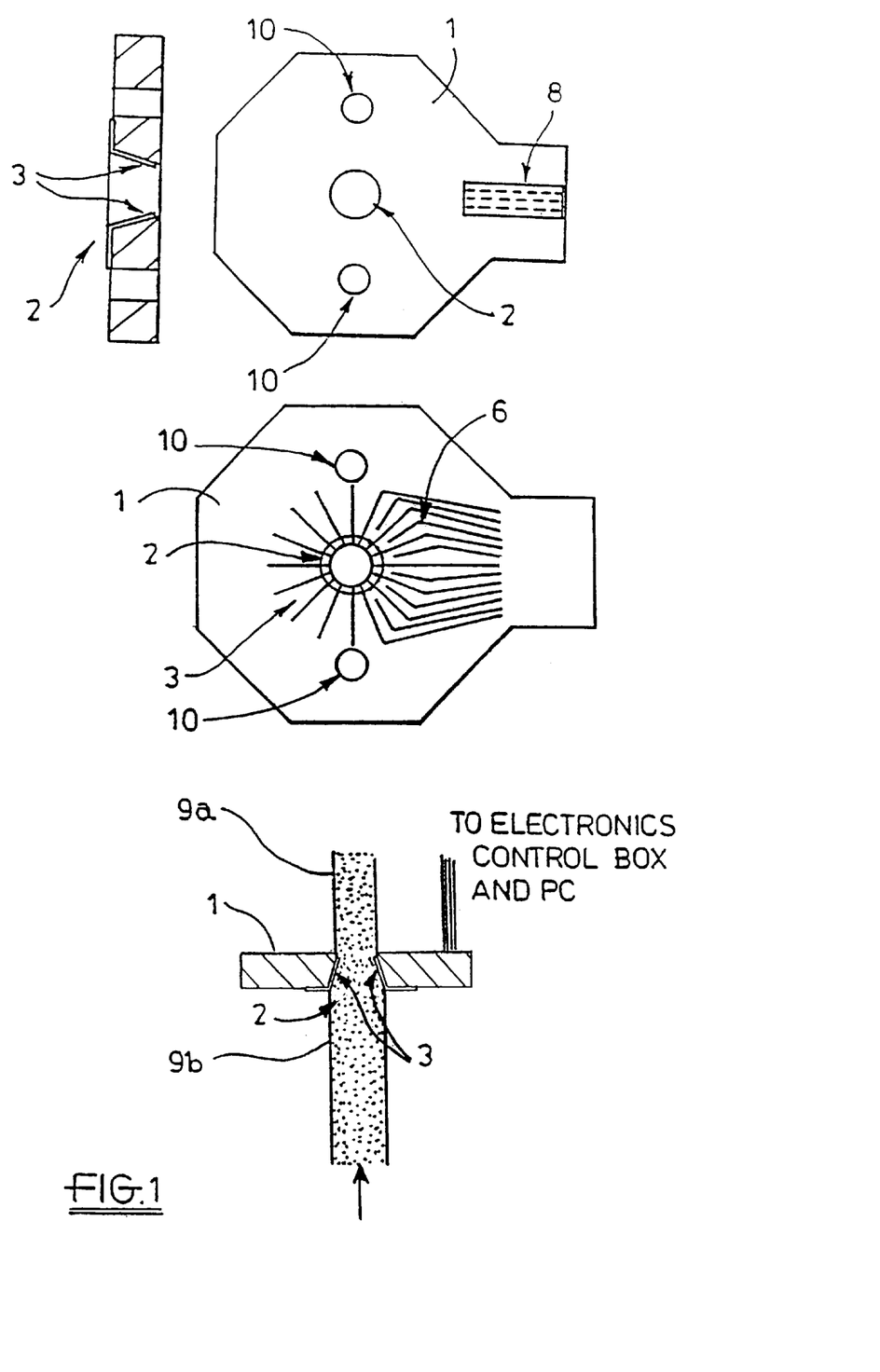
FIG. 1 shows a schematic diagram of the electrode sensor system.

Embodiments of apparatus and methods according to the invention will now be described with reference to the accompanying drawings, in which:

FIG. 1 depicts a microelectrical resistance tomography sensor comprising a substrate (1) of electrically insulating material (for example, a ceramic wafer) and having an aperture (2) bounding a fluid flow path and sensor electrodes (3) on the substrate (1) disposed around the aperture so as to contact fluid in the flow path and connected to a cable connector (8) on the substrate (1).

The electrodes (3)—which may be fabricated from a suitable conducting material, such as gold—are disposed regularly around the aperture. In this example sixteen equally spaced electrodes (3) are provided.

The sensor electrodes (3) extend into the aperture (2) and along the flow path. The aperture (2) is tapered in the direction of the flow path, providing additional area for the sensor electrodes (3). Advantageously, of course, the aperture (2) is circular, the radial symmetry simplifying the task of interpreting the conductivity data obtained.

The electrodes (3) may be printed or deposited onto the substrate (1) in any suitable manner.

The sensor also comprises guard electrodes (6) which stand between sensor electrodes (3) and terminate short of flow path fluid contact. The guard electrodes (6) are electrically connected to earth, thereby minimising electrical noise arising from crosstalk between the adjacent active electrodes (3).

An electrically insulating and water tight polymer film is placed or coated over both sides of the substrate (1). The required electrical connections to the sensor are made via the cable connector (8).

The substrate (1) is a wafer of uniform thickness, adapted for clamping between pipe sections, 9a, 9b, defining the fluid flow path. The sensor has apertures 10, displaced from the fluid flow path bounding aperture (2), which act to locate clamping means (not shown) for clamping the wafer (1) between the pipe sections 9a, 9b.

The entire microelectrical resistance tomography system comprises the sensor or a sensor arrangement (the latter option being described in more detail below) in a tube, flow means (such as a suitable pump) to flow a fluid under investigation past the sensor or sensor arrangement, and electrical control and measurement means adapted to apply selectively oscillating current to the sensor electrodes and measure electric potentials across the sensor electrodes. The basis of this approach is that selected electrodes are charged and electrical conductivities are measured. If the continuous phase and the discontinuous phase display different conductivities, then the presence of the discontinuous phase in the region of the sensor can be detected by observing conductivity perturbations. Additionally much more detailed information on the nature of the discontinuous phase can be extracted from the conductivity data.

An example of two phases having different electrical conductivities is provided by an oil (discontinuous) phase, which is non-conducting, and an aqueous (continuous) phase, which is conducting. This example is non-limiting, and in particular it should be noted that the discontinuous phase may be more conductive than the continuous phase.

Figure 2:
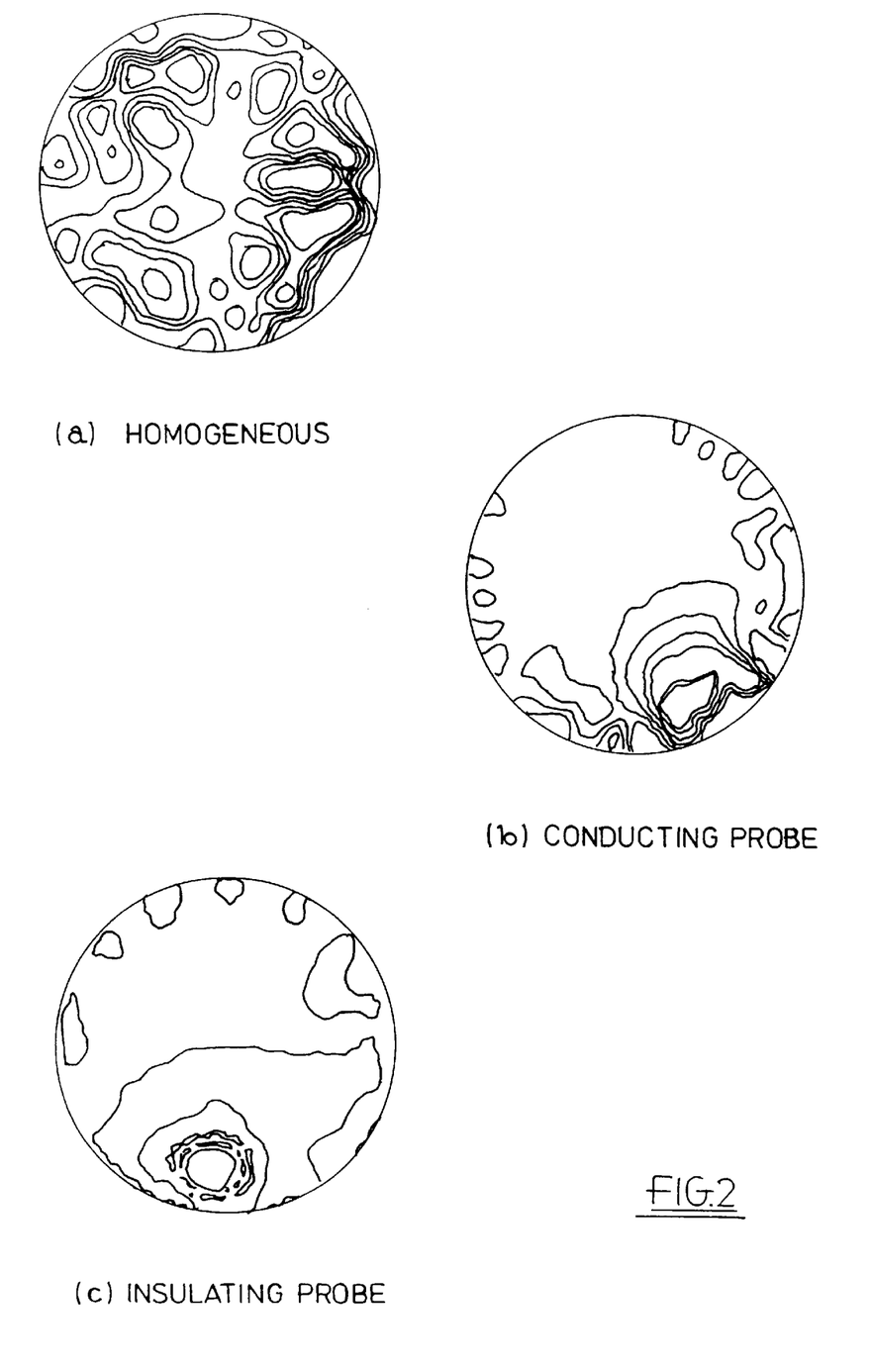
FIG. 2 shows three images obtained using a 16 electrode microsensor (a) of a homogeneous fluid in the absence of any objects, (b) in which a conducting object is being imaged and (c) in which an insulating object is being imaged, in which the actual diameter of the object being imaged is less than one tenth of the diameter of the tube.

If quantitative sizing and shape analysis of the discontinuous phase—possibly an individual droplet of oil suspended in a conducting water medium—is required, two measurement protocols may be adopted:

(i) In the first protocol, electrical currents are injected between a given pair of electrodes and the resulting voltages on the other electrodes are measured. Typically the current required may be fractions to hundreds of microamps and at one or more selected frequencies which may be 10–1000 KHz, as governed by the electrical control measurement means. The measurement procedure is repeated quickly for every possible desired combination of current injection voltage measurements involved so as to gather sufficient data to allow image reconstruction of the real and/or imaginary part of the impedance. In this way an image of the distribution of electrical properties may be obtained and such images may be acquired quickly e.g. at rates from 1–600 frames per second or more. An example of a typical image of the real part of the electrical impedance (resistivity) is illustrated in FIG. 2. The diameter of the object being imaged is less 90 $\mu$m and the diameter of the tube is 1 mm.

Figure 3:
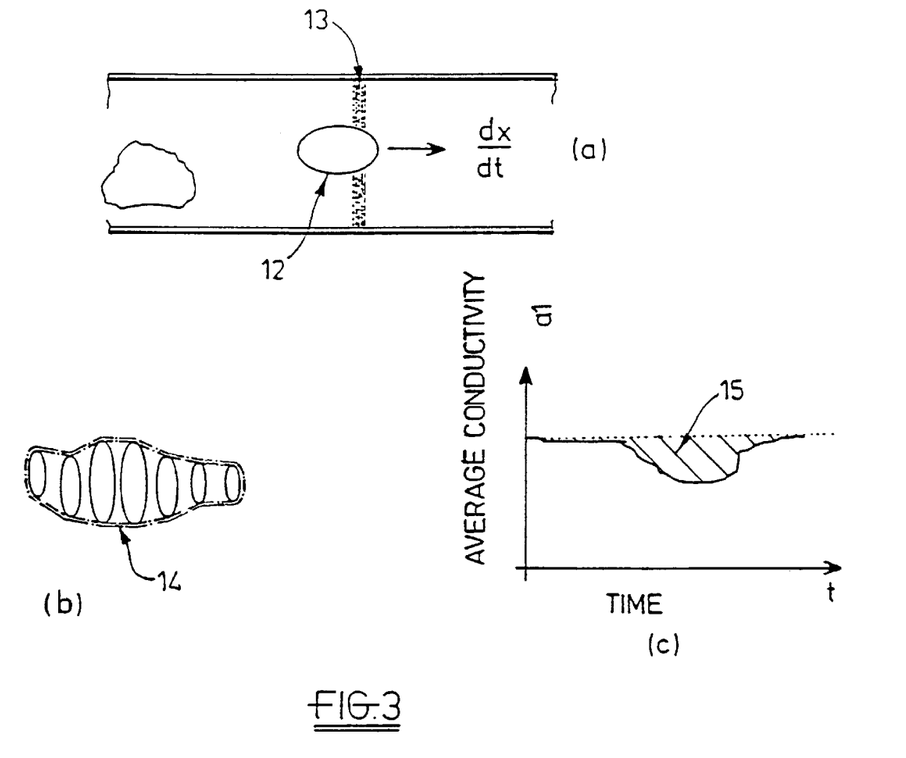
FIG. 3 shows a schematic diagram of (a) particles flowing through the sensor region, (b) the use of the electrical signals so generated to provide a three dimensional image of the particle by stacking time-spaced images, and (c) measurements of particle volume by inference from the time-varying mean conductivity within the cross-section.
Figure 4:
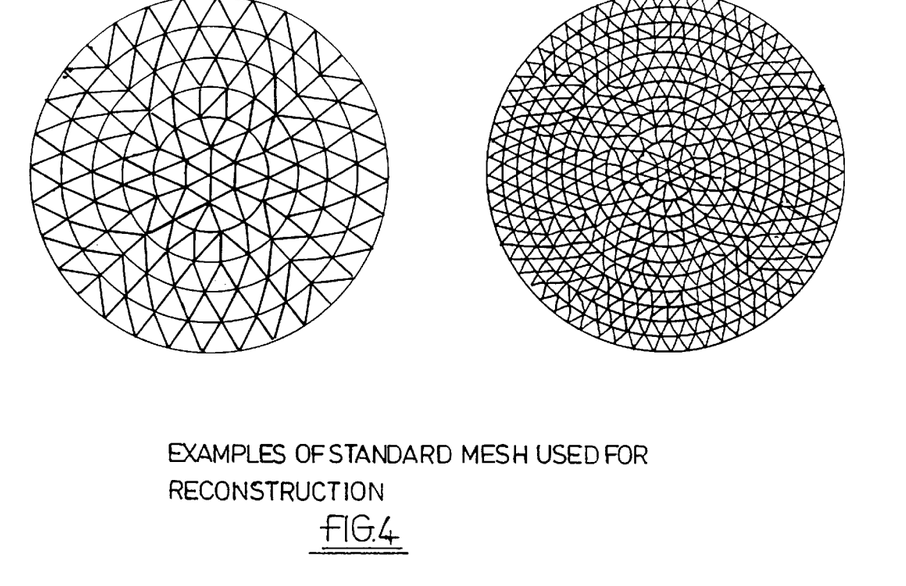
FIG. 4 shows examples of standard meshes used for reconstruction.
Figure 5:
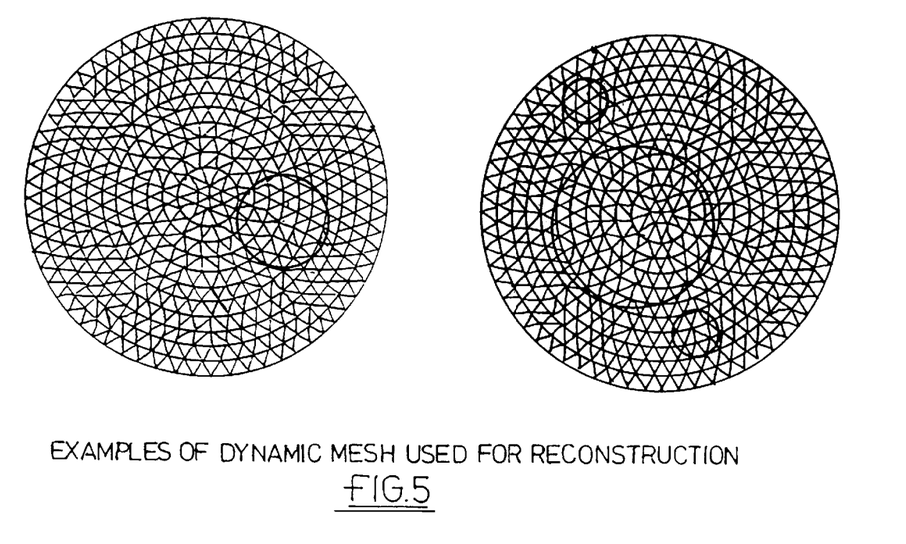
FIG. 5 shows examples of dynamic meshes used for measurement simulation.
Figure 6:
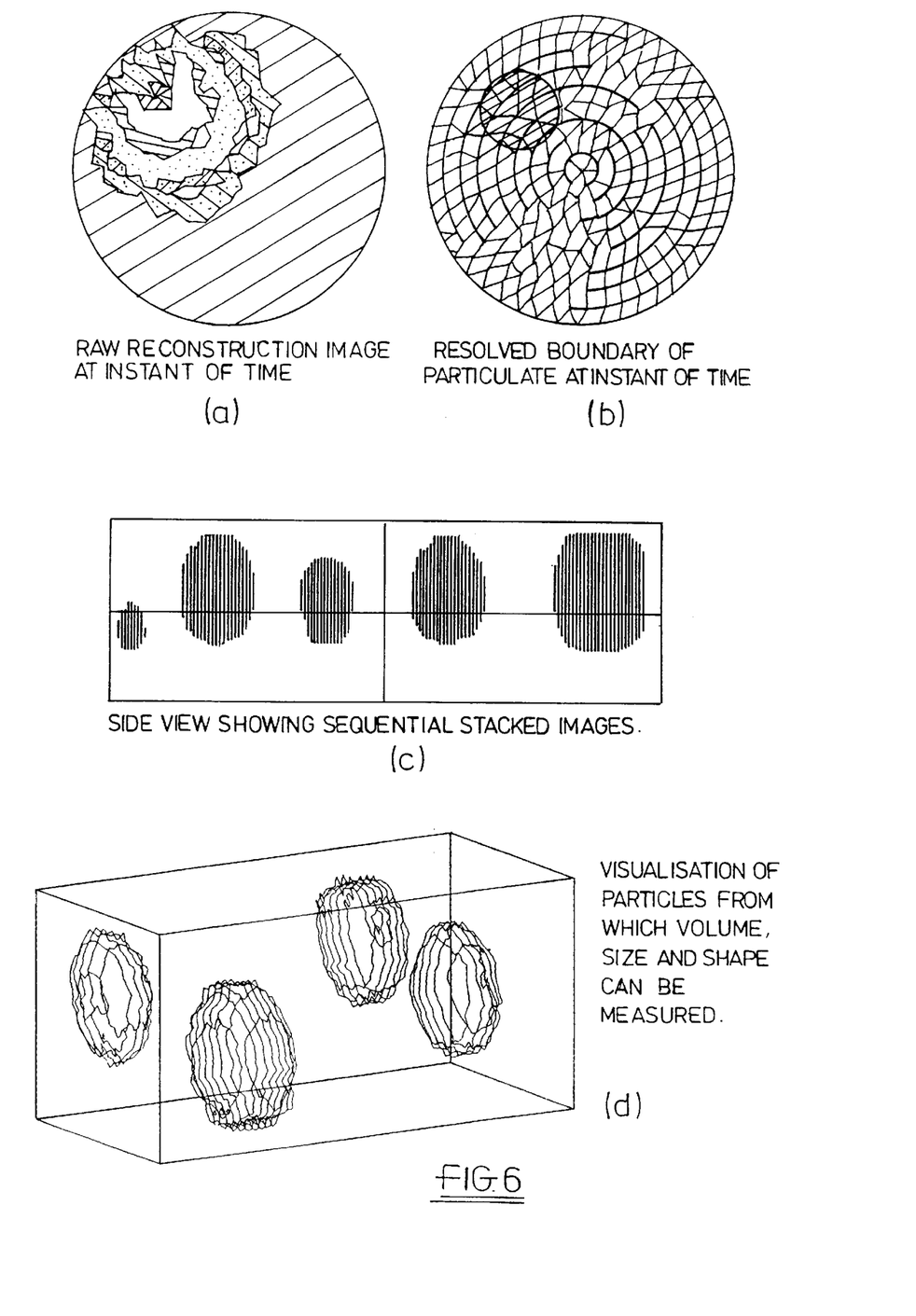
FIG. 6 shows image reconstruction for a spherical particle.
Figure 7:
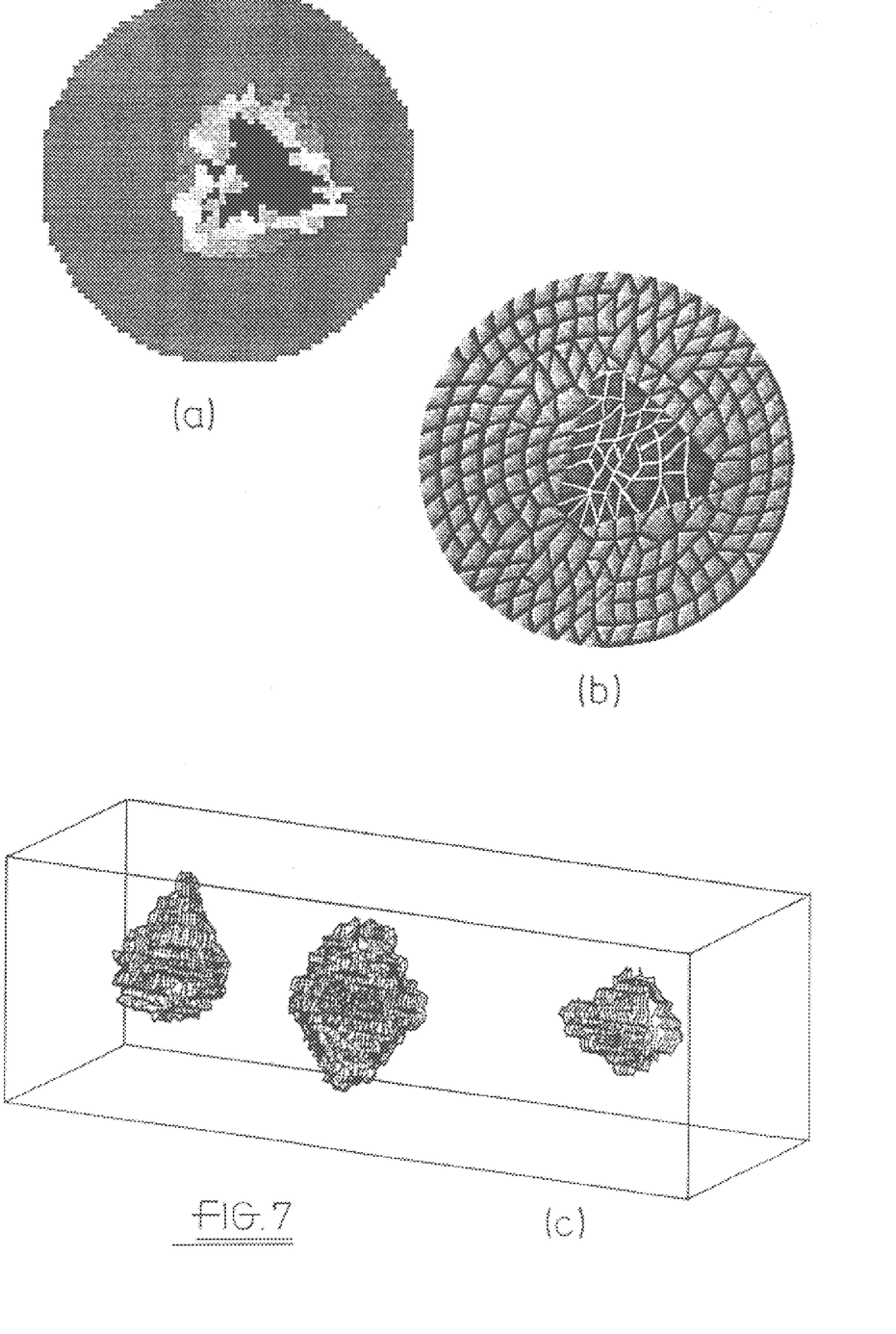
FIG. 7 shows image reconstruction for a non-spherical particle.

The present invention provides a means to size individual particles, as shown in FIG. 3, by first analysing the signals to identify the existence of an object (12) in the sensor cross-section (13) and then to obtain the best possible estimate of its size using a computer adapted with a fast qualitative reconstruction algorithm. As the particle, for example being ellipsoidal in shape, passes through the cross section it will present different apparent cross-section diameters ranging from zero up to the full diameter and then down to zero again as it leaves the sensing region. By rapidly sensing the particle boundary with time as the particle flows past the sensor and then stacking the images together and interpolating between the time-spaced frames, the true size (14) can be deduced. This is achieved by a so-called qualitative reconstruction of the data coupled with novel use of a priori knowledge, e.g. that particles are spherical, or that their shape factor is known. The reconstruction process is first attempted using a regularly-spaced finite element mesh to define what gross features are present in the image (FIG. 4). This information is then used to dynamically reconfigure the mesh (using finer grids in the regions of interest, i.e. in the vicinity of the boundary of any discontinuous phases) and the input data are rerun. The dynamic mesh is based on a Delaunay triangulation routine (see for example, Bowyer A. the Computer Journal, 24 (2) (1981) 162), which redefines the boundary of the particle and removes points of the standard mesh that lie on the apparent boundary of the particle cross-section (FIG. 5). In this way an enhanced smooth profile can be obtained. The object boundaries may then be further enhanced using a quantitative reconstruction algorithm or methods based on artificial intelligence, for example by using a neural net which can be trained to recognize features. The method of error pattern recognition provides a rapid means of improving the sizing accuracy and can be superior to conventional sensitivity methods based on error minimization routines involving mathematical iteration towards a stable best-fit solution to the measurement data. This is important since there is a critical need to perform rapid computations of many thousands of image data sets. Sequential reconstructed images from the single sensor plane can be stacked thus enabling the three dimensional shape of the object to be discerned using appropriate computer software. Examples of the procedures are shown in FIGS. 6 and 7 for spherical and non-spherical particles respectively. FIGS. 6a and 7a show the reconstructed image at a given instant of time from which (FIGS. 6b and 7b) the particle boundary can be defined (using triangulation to define the mesh or via a neural network). The images obtained at discrete intervals of time may be stacked (FIGS. 6c and 7c) and then the three dimensional boundary of the individual particles may be perceived (FIG. 6d). Size, volume, shape, surface area and other characteristics may be calculated from these images. Data on the number, volume, and specified dimensions of particles may be accumulated in the computer and used to display a historical cumulative trend of the particle size (and, if required, shape factors).

(ii) In the second method (FIG. 3c) the average conductivity in the cross section is measured using either mean conductivities computed from resistivity images, as described above, or from simpler measurement of conductivity using fewer electrodes (for example, four electrodes only) and without recourse to image reconstruction. Hence as each particle passes the sensor the particle volume (15) can be estimated from the time-integrated conductivity decrease. If the shape factor of the particle is known or the particle is known to be spherical, the mean particle diameter (or other characteristic dimensions) can be obtained. Particle volume and particle number statistics can be accumulated by the control computer, from which the size distribution can be obtained.

If more than one sensing plane is used—in other words, if a plurality of sensors are employed—information can be obtained from each image plane and cross-correlation methods can be employed to check the velocity of the particles. Further, electrical measurements can be made between electrodes in different planes. For instance the conductivity along the longitudinal axis of the pipe can be measured in addition to the cross-section conductivity. The plurality of sensors may have similar electrode configurations which, advantageously, are mutually aligned. Such arrays can be assembled by stacking together ceramic wafer sensors, each sensor being separated by a thin layer of an electrically insulating polymer.

Figure 9:
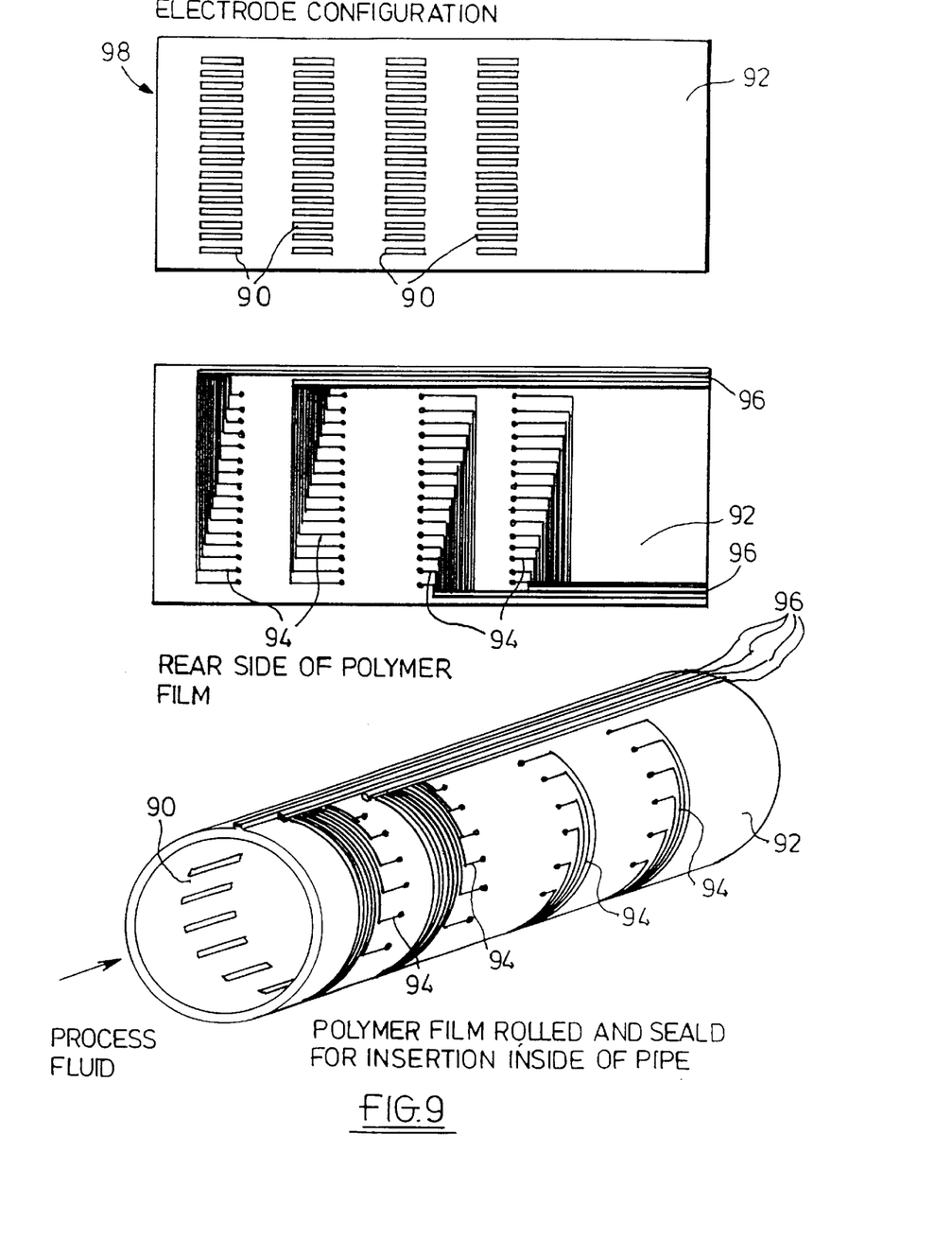
FIG. 9 shows the preparation of a monolithic sensor array.

A monolithic array 98 may be fabricated using microfabrication techniques, as illustrated in FIG. 9. Linear arrays of sensors 90 are etched from a copper. gold or silver laminated flexible polymer film 92. In the non-limiting embodiment depicted in FIG. 9. an array of four sensors, each having sixteen electrodes, is fabricated. On the other face of the polymer film 92 electrical tracks 94 are fabricated which are electrically connected to the sensors 90 in the array and to end connectors 96. The film 92 is rolled into a cylinder, sealed in this configuration and inserted into a pipe (not shown). The array of sensors 90 is on the inner surface of the pipe, with electrical connects being made via the end connectors 96 on the outside of the pipe. Suitable apertures are provided in the pipe to permit these electrical connections. If the pipe is itself conducting then suitable insulation of the electrical tracks 94 is necessary, for example by disposing a second polymer film over the electrical tracks 94. As an alternative, the array 98 may be disposed between two pipe sections in a fluid tight manner.

In the case of a dispersion containing a high volume and number proportion of particles which may present many droplets for analysis in the sensor cross section simultaneously, direct quantitative sizing may not be possible. This is often the situation in analysing a dispersed product (e.g. an oil-in-water emulsion) in a manufacturing plant. However information on particle size, shape and other flow characteristics can be obtained indirectly by inference from the electrical measurements. The present invention provides a means to characterise precisely the properties of such systems. Two types of procedures may, for example, be used with the present invention.

(i) The sensor can be used to characterize fast moving dispersions by rapid image acquisition, time-delayed reconstruction of conductivity maps, and then use of neural networks to correlate statistically time-varying features within the picture elements (pixels).

Figure 8:
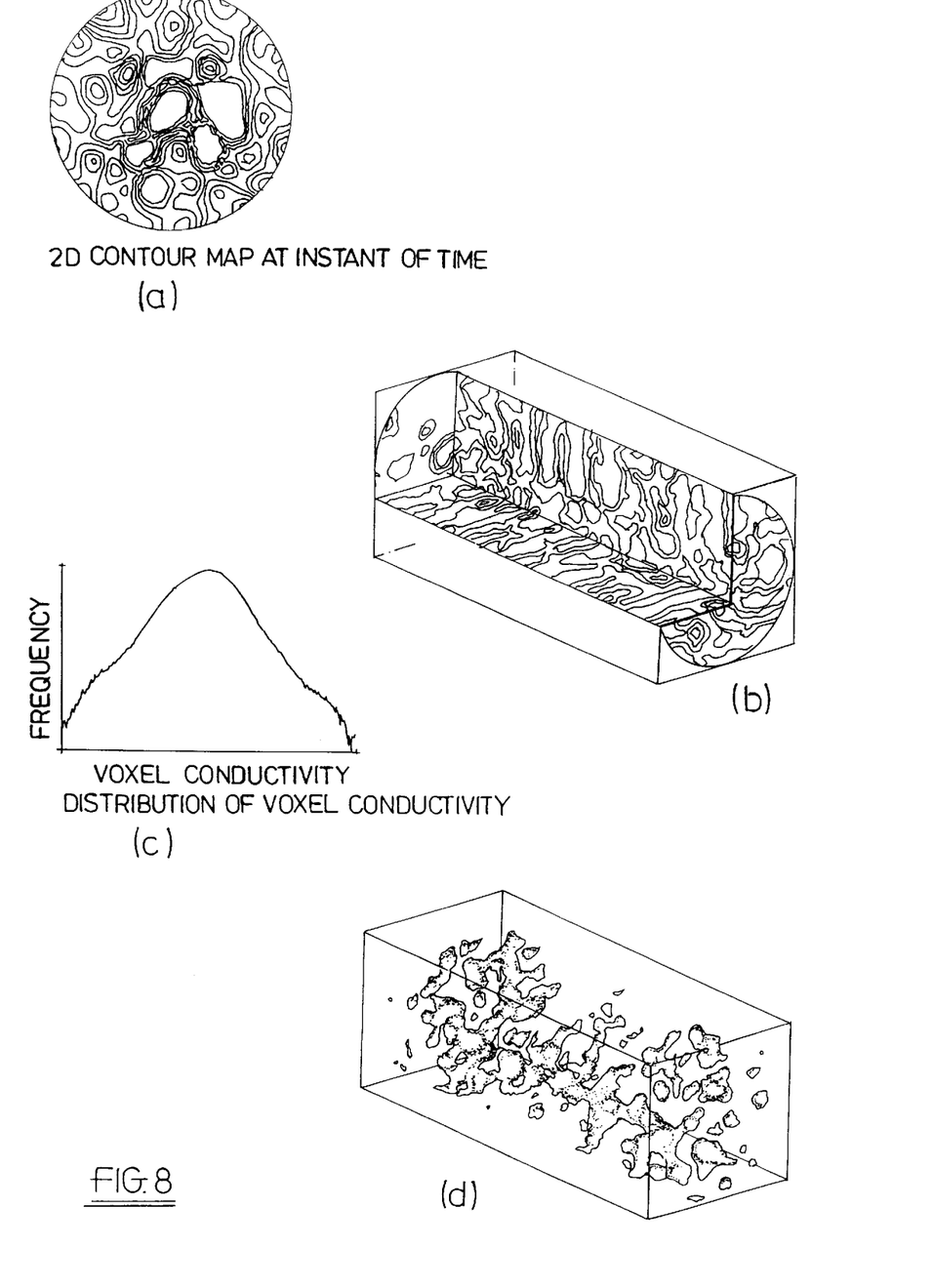
FIG. 8 shows the mapping of electrical conductivity texture of a complex dispersion.

FIG. 8 shows an example of using the method for mapping the electrical conductivity texture of a complex dispersion (oil-in-water emulsion) as it flows through a single plane of electrical sensors. Oil droplets are present as particles which differ in size and shape (some being discrete entities while others are coalesced) which in turn governs the rheological and application properties of the emulsions to the end user. By sensing the internal structure of the emulsion it is possible to gain an understanding of the quality of the emulsion being produced. For example, malfunctions in the upstream manufacturing process which may result in gross coalescence of the oil droplets or production of oil phase in different morphologies (discs, ellipsoids etc) can be detected on-line and remedied via a feed back control mechanism. For example. FIG. 8a shows a conductivity image across the sensor plane at a given instance of time; by repeating the measurement as the emulsion flows through the sensor a time-spaced map can be rendered (FIG. 8b) by interpolating between the time-spaced images. Regions of different conductivity can be seen within this, now, three dimensional map.

This textural information can be interpreted by analysing the statistics of these textural features. This may be achieved for instance, by using a neural net model in which the inputs to the net are values derived from the texture map based on simultaneous use of two data sets derived from the voxels (typically more than 500 consecutive time spaced images must be examined), as shown in FIG. 8c and FIG. 8d. In one example, five input values are derived, namely, the statistical mean, standard deviation, kurtosis and skewness of the distribution of the conductivity in each voxel (FIG. 8c). Next, a further five inputs are derived by selecting the boundaries of regions in the 3D texture which have a specified conductivity (FIG. 8d). The specified conductivity may select, for example, regions where the conductivity is greater than 10% above the overall mean conductivity throughout the entire sample. (The actual value chosen is determined according to the features being sought and the specific electrical properties of the flowing mixture.) The five inputs may be, but are not limited to, the number of regions per unit volume, the total volume of the regions of interest, the ratio of the measured volume to the calculated surface area of the regions, and the mean spacing between regions in the radial and axial directions. The net can be used to correlate these inputs to emulsion properties including rheological parameters (viscosity), mixture composition and customer acceptance factors (e.g. in the case of a food emulsion, indices relating to the feel, taste, odour, edible texture, appearance etc).

If a plurality of sensors is employed, it is possible to cross-correlate signals from time-spaced pixels in the image planes, and hence derive information on the velocity distribution in the pipe. By cross-correlating only those features or regions of interest (FIG. 8d), the frequency at which those features are appearing in the pipe and their velocity can be estimated.

A simpler alternative procedure can be adopted which does not require a full conductivity image to be reconstructed (which is computationally demanding). By acquiring the raw voltage readings between selected electrode pairs (or projections) at high sampling frequency, these data can be used as inputs to a neural net model. These measurements may be made within and/or between electrode planes, in the case of a three dimensional assembly of electrode sensors. The method of correlating these signals is similar to that described above. This is an "on-line" model such that it learns to recognize features in the voltage patterns and to correlate these features to known process characteristics. Dynamic multivariate statistical methods can also be used to exploit the temporal variations in the signals, which reveal information on the degree of uniformity of the discontinuous phase size polydispersity, number concentration, flux etc. This affords a means to monitor the dispersion manufacturing processes for the purpose of process control and to provide a means to correlate the dispersion properties with other information such as the acceptability of the product to the end-user (e.g. the customer).

(ii) Concentrated dispersions and suspensions which contain anisotropic particles often change their structural characteristics if the flow velocity is changed. For example, high aspect ratio particles (rods, platelets) tend to align in the flow. Hence by causing the flow within the tube to vary in a linear (e.g. successively increase flow velocity) or discontinuous wave (e.g. to stop the flow instantaneously) and monitoring the change in electrical properties using one of the above mentioned methods, further insight into the particle shape and size can be gained. This can be used to monitor changes in particle shape.

Examples of applications for the apparatus and methods described above include:

(i) the detection of flow or obstructions to flow in tubes such as blood vessels, ink jets, spray dryers and aerosols;

(ii) determining the nature of mixture flow in narrow tubes. Examples include blood vessels, polymer extrusion, food extrusion—such as cheese—and the formulation of dispersions, emulsions and gels;

(iii) metering/dosing applications whereby the method is used to monitor the discharge of liquid into another process; and (iv) detection of foreign bodies present in products flowing in tubes (e.g. oil droplet contamination in liquid effluents and debris in foodstuffs).

What is claimed is:

1. A microelectrical resistance tomography system comprising a sensor including a wafer substrate of electrically insulating material having an aperture bounding a fluid flow path through a tube and more than two sensor electrodes on the substrate disposed circumferentially around the aperture so as to contact fluid in the flow path and connected to a cable connector on the substrate, flow means to flow a fluid under investigation through the tube past the sensor, and electrical control and measurement means for applying selectively oscillating current to the sensor electrodes and measuring electric potentials across the sensor electrodes.

2. A system according to claim 1, in which the sensor electrodes are uniformly spaced around the aperture.

3. A system according to claim 1, in which the sensor electrodes extend into the aperture and along the flow path.

4. A system according to claim 1, in which the aperture is circular.

5. A system according to claim 1, in which the sensor electrodes are printed on to the substrate.

6. A system according to claim 1, comprising guard electrodes which stand between sensor electrodes.

7. A system according to claim 6, in which the guard electrodes terminate short of flow path fluid contact.

8. A system according to claim 6, in which the guard electrodes are electrically connected.

9. A system according to claim 8, in which the guard electrodes are earthed.

10. A system according to claim 1, in which the substrate is of uniform thickness and is clamped between pipe sections of the tube defining the fluid flow path.

11. A system according to claim 10, having additional apertures displaced from the fluid flow path bounding the aperture.

12. A system according to claim 1, wherein the flow means comprises fluid flow control means for controlling fluid flow through the tube.

13. A system according to claim 1, comprising analysis means for analyzing the electric potentials measured by the control and measurement means.

14. A system according to claim 13, in which said analysis means comprises tomographic image store means for storing a succession of tomographic images of a flowing fluid.

15. A system according to claim 13, in which said analysis means comprises computer means evaluating image data in accordance with predetermined algorithms.

16. A system according to claim 13, in which said analysis means comprise a neural net.

17. A system according to claim 1, in which the aperture in the substrate is tapered in the direction of the fluid flow path.

18. A system according to claim 1, comprising a sensor arrangement including a plurality of the sensors in the tube, the flow means causing fluid under investigation to flow through the tube past the sensor arrangement, the electrical control and measurement means applying selectively oscillating current to the sensor electrodes and measuring electric potentials across the sensor electrodes.

19. A sensor arrangement for microelectrical resistance tomography comprising a polymeric film substrate having an aperture bounding a fluid flow path, and a plurality of microelectrical resistance tomography sensors disposed on the substrate along the fluid flow path, each of the sensors comprising more than two sensor electrodes disposed circumferentially around the aperture so as to contact fluid in the flow path.

20. A sensor arrangement according to claim 19 in which the polymeric film substrate is flexible and is rolled so as to substantially define a cylinder forming the aperture bounding the fluid flow path.

21. A sensor arrangement according to claim 19 in which the sensors comprise a monolithic array.

22. A sensor arrangement according to claim 21 in which the polymeric film substrate is laminated and the sensors are formed by etching the laminated polymeric film substrate.

23. A method for characterizing a non-homogeneous flow of flowing material comprising the steps of passing the flowing material through a tube having a plurality of sensors disposed along the tube, each of the sensors comprising a plurality of electrodes disposed circumferentially around the flow, and making electrical measurements between the electrodes of different ones of the sensors.

24. A method according to claim 23 comprising the further step of making additional electrical measurements between the electrodes of a common sensor.

25. A method according to claim 24 in which the additional electrical measurements are tomographic measurements.

26. A method according to claim 24 comprising the further steps of injecting oscillating current into the flow via selected ones of the electrodes and measuring the voltage response on other of the electrodes.

27. A method according to claim 24 in which the additional electrical measurements are measurements of microelectrical resistance tomographic measurements.

28. A method according to claim 24 in which the additional electrical measurements are average electrical conductivities.

29. A method according to claim 24, in which the measurements, or quantities related to or derived therefrom, are analyzed by a neural net.

30. A system for characterizing a non-homogeneous flow of flowing material comprising means for flowing material through a tube having a plurality of sensors disposed along the tube, each of the sensors comprising a plurality of electrodes disposed circumferentially around the flow, and electrical measurement means for making electrical measurements between the electrodes of different ones of the sensors.

31. A system according to claim 30 wherein the electrical measurement means makes additional electrical measurements between the electrodes of a common sensor.

32. A system according to claim 31 in which the additional electrical measurements made by the electrical measurement means are tomographic measurements.

33. A system according to claim 31 comprising means for injecting oscillating current into the flow via selected ones of the electrodes and measuring the voltage response on other of the electrodes.

34. A system according to claim 31 in which the additional electrical measurements made by the electrical measurement means are measurements of microelectrical resistance tomographic measurements.

35. A system according to claim 31 in which the additional electrical measurements made by the electrical measurement means are average electrical conductivities.

36. A system according to claim 31 comprising a neural net for analyzing the measurements, or quantities related to or derived therefrom.

37. A system according to claim 30 wherein each of the sensors comprises more than two electrodes disposed circumferentially around the flow.

* * * * *